United States Patent [19]

Müller

[11] Patent Number: 5,026,732

[45] Date of Patent: Jun. 25, 1991

[54] USE OF AVARONE FOR THE CONTROL OF AIDS AND ARC

[75] Inventor: Werner E. G. Müller, Wiesbaden-Biebrich, Fed. Rep. of Germany

[73] Assignee: Merz + Co. GmbH & Co., Frankfurt (Main), Fed. Rep. of Germany

[21] Appl. No.: 458,892

[22] Filed: Dec. 29, 1989

Related U.S. Application Data

[60] Division of Ser. No. 58,200, Jun. 4, 1987, Pat. No. 4,939,177, which is a continuation-in-part of Ser. No. 820,440, Jan. 17, 1986.

[30] Foreign Application Priority Data

Jun. 7, 1986 [DE] Fed. Rep. of Germany ....... 3619202

[51] Int. Cl.$^5$ ............................................. A61K 31/12
[52] U.S. Cl. ..................................................... 514/691
[58] Field of Search ................................ 514/691, 661

[56] References Cited

PUBLICATIONS

Kurelec et al., Mutation Research, 144 (1985), pp. 63–66.

Muller et al., Cancer Research, 45, pp. 1–5 (Oct. 1985).

Primary Examiner—Jerome D. Goldberg
Attorney, Agent, or Firm—Gordon W. Hueschen

[57] ABSTRACT

The invention concerns the use of avarone and pharmaceutical compositions thereof for the control of AIDS and AIDS-Related Complex (ARC).

2 Claims, No Drawings

USE OF AVARONE FOR THE CONTROL OF AIDS AND ARC

This application is a division of prior-filed copending application Ser. No. 058,200, filed June 4, 1987, now U.S. Pat. No. 4,939,177 which in turn is a continuation-in-part of application Ser. No. 820,440, filed Jan. 17, 1986.

The present invention relates to the use of avarone for the control of AIDS and ARC.

Avarone and its hydroquinone derivative (avarol) are natural substances which are present in the marine sponge Dysidea avara[1]. Federal Republic of Germany OS 34 27 383, published Jan. 30, 1986, describes that avarone and avarol and its derivatives have antitumoral, antibacterial and antimycotic properties which make them appear suitable, in particular, for the treatment of cancer and infectious diseases. Furthermore, it is stated therein that these compounds have a certain virostatic action in vitro against cultures of herpes simplex virus and therefore against DNA viruses. However, no data has been heretofore available concerning the possible inhibition of RNA viruses.

[1] Tetrahedron Letters 1974, 3401-3404; J. Chem. Soc. Perkin I, 1408-1414 (1976).

In addition to this, it has been found that avarone and its derivatives have antimutagenic activity[2]. Finally, it has been discovered that avarone and its derivatives also have an antileukemic action[3]. The existence of this antileukemic action has been derived from studies in vitro as well as in vivo with mouse leukemia cells L5178-Y. Up to the present time, however, no virus causality in the case of tumors is known on the part of these leukemia cells. Therefore, it was not obvious to use avarone or the derivatives thereof for the control of the virus-produced clinical picture of AIDS.

[2] Mutation Research 144, 63-66 (1985).
[3] Cancer, Res. 1985; 45 (10), 4822-4826.

The object of the present invention is to provide a promising method of controlling AIDS or AIDS-related complex (ARC).

AIDS is caused by the human T-cell leukemia/lymphotropic virus of type III (HTLV-III)[4], which is also known as lymphadenopathy-associated virus (LAV)[5]. HTLV-III belongs to the type of RNA viruses which differ in essential points from the DNA viruses. The viral attack is the main cause of a spectrum of immunological disturbances of which AIDS manifests itself clinically most severely in the form of Karposi's sarcoma or of AIDS-Related Complex (ARC)[6]. Up to now, no effective therapeutic treatment of AIDS or ARC has been possible.

[4] Science, 224, 500-502 (1984).
[5] Science, 225, 69-72 (1984).
[6] Proc. Natl. Acad. Sci. USA, 82, 5530-5534 (1985).

It has surprisingly now been found that avarone is excellently suited for controlling acquired immunodeficiency syndrome (AIDS) or AIDS-Related Complex (ARC).

The object of the invention therefore is the use of avarone for the control of AIDS and ARC.

The preparation of avarone is described in Federal Republic of Germany OS 34 27 383. For this the marine sponge Dysidea avara is extracted with ethyl acetate. Avarone is recovered from the extract by column chromatography on silica gel. Avarone can also be prepared from avarol by oxidation with silver oxide.

The compound which is to be used in accordance with the invention is generally employed in the form of pharmaceutical compositions which are produced in the form of dosage units and can be administered systemically, i.e., orally, rectally, or parenterally (intramuscular, intravenous and subcutaneous).

The compositions contain avarone in an amount effective for the treatment, elimination, alleviation, or improvement of AIDS or ARC or in an immunity-defect eliminating amount, possibly together with a pharmaceutically compatible excipient and/or adjuvant. Such pharmaceutical agents contain, for instance, 0.5 to 98 wt. % of the compound of the invention, together with a pharmaceutical excipient.

If the agent is present in the form of a dosage unit, it preferably contains 10 to 100 mg of the compound used in accordance with the invention.

The pharmaceutical agents can be present, for oral administration in solid form, for instance, as tablets, pastilles, capsules or powder, or in liquid form, for instance, as aqueous or oil suspensions, syrup, elixir, solution or liquid-filled capsules.

Preferred oral agents are in the form of tablets or capsules and can contain ordinary excipients such as binders (for instance, syrup, acacia, gelatin, sorbitol, tragacanth or polyvinylpyrrolidone), fillers (for instance, lactose, sugar, corn starch, potato starch, calcium phosphate, sorbitol or glycine), lubricants (for instance, magnesium stearate, talc, polyethylene glycol or silica), disintegration agents (for instance, starch) and wetting agents (for instance, sodium lauryl sulfate).

Agents for parenteral administration are in general in the form of a solution or suspension of the compounds used in accordance with the invention together with ordinary pharmaceutical excipients, for instance, in the form of an aqueous solution for intravenous injection or of an oil suspension for intramuscular injection. Agents suitable for parenteral administration are obtained by dissolving 0.1 to 10 wt. % of the compounds of the invention in water or an excipient which consists of an aliphatic polyalcohol such as glycerin, propylene glycol or polyethylene glycols or mixtures thereof. The polyethylene glycols consist of a mixture of non-volatile, ordinarily liquid polyethylene glycols which are soluble both in water and in organic liquids and the molecular weights of which range from 200 to 1500.

Pharmaceutical agents for rectal administration are in the form of suppositories, the compounds of the invention being incorporated in a suitable suppository base such as cocoa butter, hydrogenated fats, polywaxes or polyethylene glycols, in an amount of 1 to 10% by weight.

The pharmaceutical agents are prepared by ordinary methods, for instance, by tabletting, incorporating of the compounds used in accordance with the invention in a suppository base, sterile filtration and filling in ampules or dropper bottles of a solution of the compounds used in accordance with the invention in water for injection together with ordinary additives such as sodium chloride, sodium dihydrogenphosphate, disodium edetate (ethylene diaminotetraacetic acid disodium salt), benzyl alcohol or sodium hydroxide in order to adjust the pH.

The procedure for the treatment of AIDS or ARC comprises the administration of a therapeutically (antivirally or immunomodulating or prophylactically) active amount of avarone to a patient who requires this treatment.

The dose depends primarily on the specific form of administration and the purpose of the therapy. The size of the individual doses as well as the program for administration can be determined best on basis of an individual evaluation of the specific case by the doctor, in which connection the age, weight and condition of the patient, the route of administration and the nature and severity of the illness must be taken into account. In general, the daily dose is 2 to 20 mg/kg of body weight and preferably 3 to 10 and particularly 6 to 7.

The duration of the treatment depends on the nature and severity of the disease. It extends in general over several weeks, for instance, 4 to 8 weeks.

The compound selected to be used in accordance with the present invention acts in a diversified manner against human T-cell leukemia virus of type III (HTLV-III) and they produce a stimulating action on the immune system so that the endogenous defense forces against AIDS, AIDS-related complex (ARC) and related illnesses are reinforced. The compound can therefore be used for the therapeutic and prophylactic treatment of the diseases caused by the AIDS virus.

The activity of the compound used in accordance with the invention will be examined below on basis of pharmacological in-vitro test systems using avarone as example.

For this, the H9 cell line was used, it consisting of a cloned OKT4+ T-cell line in which the AIDS virus propagates (M. Popovic, M. G. Sarngadharan, E. Reed and R. C. Gallo; Science 224, 497–500 (1984)).

Test Procedure:

Purification of HTLV-III reverse transcriptase and assay conditions:

The HTLV-III reverse transcriptase used for the present experiments (prepared by the method of P. S. Sarin, Y. Taguchi, D. Jun, A. Thornton, R. C. Gallo, B. Oeberg, Biochem. Pharmacol. 34, 1985, pages 4075 to 4079) was purified by sequential chromatography on DEAE-cellulose, phosphocellulose and hydroxyapatite. The purified enzyme was stored in 50 mM tris-HCl (trishydroxymethylaminomethane) (pH 7.5), 1 mM dithiothreitol (DTT), 0.01% Triton X-100 and 20% glycerin. The assays for reverse transcriptase were carried out in a reaction mixture (50 μl) which contained 50 mM tris-HCl(pH 7.5), 5 mM DTT, 10 mM MgCl$_2$, 100 mM potassium chloride, 0.01% Triton X-100 ($C_8H_{17}$-$C_6H_4$-$(OCH_2CH_2)_{9\text{-}10}$-OH) or NP40 (non-ionic detergent Nonidet P 40, brand name of the Sigma company, i.e., octylphenol ethylene oxide condensate), 10 μg/ml (dT)$_{15}$·(A)$_n$ (hybrid polymers of the oligo- or polynucleotides oligodeoxythymidylic acid and polyadenylic acid) as template primer and [$^3$H]-deoxythymidine triphosphate ([$^3$H]-dTTP). The reaction mixture was incubated for one hour at 37° C. and the reaction was stopped by adding 50 μg of yeast-tRNA and 2 ml of a 10% trichloroacetic-acid solution (TCA) containing 1 mM of sodium pyrophosphate. The samples were filtered through a millipore filter (0.45 μm), and washed, first with 5% TCA-solution (5x) and then with 2 ml of 70% ethanol. The filters were dried under a heating lamp, whereupon scintillation liquid was added and the radioactivity was determined in a beta-scintillation counter.

HTLV-III Infection of H9-cells:

H9-cells (M. Popovic, M. G. Sarngadharan, E. Reed, R. C. Gallo, Science: 224, 1984, 497–500) were treated with Polybren ® (hexadimethrinbromide available on the market; 2 μg/ml) for 30 minutes at 37° C., washed free of Polybren and infected with $2 \times 10^8$ HTLV-III virus particles (isolated from H9 cell cultures by the method of M. Popovic; see above) per $4 \times 10^5$ H9 cells. Some assays which were not treated with drugs were used as positive controls, while different concentrations of the compound to be tested (avarone or avarol and their derivatives) were added to the test samples. The HTLV-III reverse transcriptase activity of these cultures was analyzed in the manner described above.

Immunofluorescence Assay:

The immunofluorescence assays were carried out on methanol:acetone (1:1)-fixed cells with the use of monoclonal antibodies (from the mouse) against HTLV-III p15 (core protein of MW=15,000) and p24 (core protein of MW=24,000). Both of these proteins are marker proteins which indicate the presence of virus particles in the cells. The HTLV-III infected cells with or without drug treatment were fixed on toxoplasmosis slides. After fixation with methanol-acetone (1:1) for 30 minutes at room temperature, the slides were stored in sealed plastic containers at −20° C. until use. The monoclonal antibodies were added to the cells, incubated at room temperature in a moisture chamber for one hour and washed for two hours with PBS (phosphate buffered saline) containing 0.25% Triton X-100. The cells were then treated for one hour with fluorescein (FITC) labeled goat anti-mouse IgG (Capell Labs.) and washed overnight with PBS buffer containing 0.25% Triton X-100. Fifty percent glycerin was added to the slides and the cell fluorescence was determined with a Zeiss fluorescence microscope.

1. Cell Growth:

H9-cells as well as H9-cells infected with HTLV-III were used in a concentration of $0.2 \times 10^6$ cells/ml of culture medium for the inoculating of a culture medium. After incubation for four days, the density of the H9-cells was $1.3 \times 10^6$ cells/ml, while the density of the H9-cells infected with HTLV-III was only $0.5 \times 10^6$ cells/ml; these two values formed the control values.

Thereupon samples of H9-HTLV-III cells, $0.2 \times 10^6$ cells/ml, were treated for four days with different concentrations of avarone. The following results were obtained:

|  | Concentration of the drug (μg/ml) | Cell Concentration $\times 10^6$/ml |
|---|---|---|
| Control-infected cells | 0 | 0.5 |
| Avarone (infected cells) | 0.1 | 1.36 |
|  | 1 | 0.17 |
| Control-uninfected | 0 | 1.3 |

It is clear that avarone in the concentration of about 0.1 μg/ml increases the growth rate of H9-HTLV-III cells to values which lie within the range of the control, namely of the H9-cells without HTLV-III. With avarone concentrations of more than 1 μg/ml toxic effects could be noted.

2. Inhibition of the Production of Reverse Transcriptase by H9-HTLV-III cells which were treated with avarone:

It was examined whether the four-daY addition of avarone to H9-HTLV-III cells stops the production of HTLV-III viruses. Reverse transcriptase was selected as measure for the amount of virus in the culture medium. Therefore, inhibition of the reverse transcriptase indicates inhibition of the production of virus. The results are set forth in the following table:

| Compound added | Concentration of the compound ($\mu$g/ml) | Reverse Transcriptase activity (in %) |
| --- | --- | --- |
| None | — | 100 |
| Avarone | 0.1 | 20 |
| | 1 | 14 |
| | 5 | 14 |

It is clear that, in the supernatant of the H9-HTLV-III cells which were not treated with avarone, a considerable activity of reverse transcriptase was indicated. The addition of avarone led to a dose-dependent reduction of the reverse transcriptase activity in the supernatant. Even with a very low dose of 0.1 $\mu$g/ml, a considerable inhibition was noted. The compound used in accordance with the invention is therefore able to inhibit virus replication practically completely at doses in which various in vitro parameters, for instance, cell growth, are practically not detrimentally affected.

3. Inhibition of HTLV-III p15 and p24 expression in H9-HTLV-III by avarone:

It was found that avarone possesses a strongly inhibitory action on the expression of HTLV-III p24 and p15 in infected H9-cells. When the target H9-cells were treated with the HTLV-III isolate and cultivated without the compound to be tested, the H9-cells were infected and, as established by indirect immunofluorescence assay, there was expression of the p24 and p15 protein. After incubation of the H9-HTLV-III cells with the compound to be tested, a practically complete protective effect was observed. The following results were obtained:

| Compound added | Concentration of the compound ($\mu$g/ml) | Expression of p15 and p24 (in %) | |
| --- | --- | --- | --- |
| | | p15 | p24 |
| None | — | 100 | 100 |
| Avarone | 0.1 | 50 | 70 |
| | 1 | 37 | 70 |

It is clear that avarone caused a significant reduction in the expression of the HTLV-III proteins p15 and p24.

Toxicity

The in-vivo toxicity (mg compound/kg) of avarone in male NMRI mice is as follows:
Acute toxicity: $LD_{50}$ 181.2, $LD_{10}$ 111.1
Subacute toxicity: $LD_{50}$ 172.1, $LD_{10}$ 109.7
(Müller et al., Cancer Research 1985, 45, 4822–4826).

IDENTITY

The active antiviral and antitumor ingredient or agent of the present invention has the formula:

Avarone

2-[(1R)-1,2,3,4,4a,7,8,8a$\alpha$-octahydro-1B,2B,4aB,5-tetramethyl-1-naphtylmethyl]-quinone

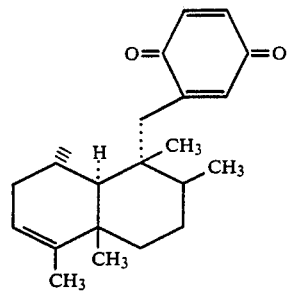

Molecular Formula of Avarone $C_{21}H_{28}O_2$; Mol wt: 312.20
C 80.73%; H 9.03%; O 10.24%

The compound 3,4-dihydroavarone is readily synthesized as follows:

Synthesis of 3,4-Dihydroavarone from 3,4-Dihydroavarol

Three-tenths gram (0.3 g) of 3,4-Dihydroavarol is dissolved in ten (10) ml of diethylether and added to 0.25 g of silver oxide. After mixing for two (2) hours, the reaction mixture is filtered and the filtrate is supplemented with two (2) g of sodium sulfate. After standing overnight, the sodium sulfate is removed by filtration. The 3,4-dihydroavarone formed is obtained in purified form by crystallization from n-hexane.

PRODRUGS OR PRECURSORS AND THEIR PREPARATION

The compound avarone and its 3,4-dihydro derivative may also be employed or embodied in pharmaceutical compositions according to the invention and administered in the form of compounds which convert or metabolize thereto after introduction into the living animal body. Such compounds are commonly referred to today as prodrugs or precursors, and representative examples include their esters and alkylamino derivatives. As already indicated, some of these compounds are known in the prior art, whereas others are made in a known manner corresponding thereto. Representative of such prodrugs and precursors, and their preparation, are set forth in the foregoing and in the following.

The following Examples serve to explain the invention, but are not to be construed as limiting.

EXAMPLE 1

Avarone and avarol 3 kg of fresh sponge (water containing) are crushed in a Starmix TM mixer and extracted with 250 ml of ethyl acetate; the extract thus obtained is dried over magnesium sulfate and then filtered. The filtrate is concentrated to dryness. The remaining residue (about 50 g) is taken up in about 100 ml of benzene and chromatographed over a silica-gel column (about 200 g) with benzene as eluent. Avarone appears in the eluate while avarol remains in the column. Avarol is eluted with a mixture of benzene and ethyl acetate (90:10, V:V). The eluate is concentrated to dryness and avarol then obtained in pure form by crystallization from dichloromethane-acetone. Avarone is purified by recrystallization from benzene. Yield: 0.7 g avarone; 8.9 g avarol; avarone MP: 62°–64° C.; avarol MP: 148°–150° C.

EXAMPLE 2

3′-ethylamino-avarone and 4′-ethylamino-avarone a) 2.5 g of ethylamine hydrochloride and 5 ml of pyridine are added to a solution of 500 mg of avarone and 1000 ml of 50% ethanol and after 20 hours the ethanol is distilled off under the vacuum of a water-jet pump. The aqueous residue is extracted with dichloromethane and the concentrated dichloromethane extract is chromatographed over a silica-gel column (about 30 g) with dichloromethane as eluent. In this way it is possible to separate the 3′-ethylamino-avarone and 4′-ethylamino-avarone; yield 480 mg and 420 mg respectively.

In similar manner there were obtained:
b) 3′-propylamino- and 4′-propylamino avarone
c) 3′-isopropylamino and 4′-isopropylamino avarone
d) 3′-n-butylamino and 4′-n-butylamino avarone.

Examples of Pharmaceutical compositions

In the following examples of formulations there can be used as active substance in each case one of the compounds used in accordance with the invention by itself or in mixture with another compound according to the invention.

Example a

| | Tablet Formulation |
|---|---|
| Active substance* | 10 mg |
| Lactose | 18 mg |
| Potato starch | 38 mg |
| Gelatin | 2 mg |
| Talc | 2 mg |
| Magnesium stearate | 0.1 mg |

*e.g., avarone or prodrug or procursor thereof

Example b

| | Tablet Formulation |
|---|---|
| Active substance* | 10 mg |
| Potato starch | 40 mg |
| Polyvinylpyrrolidone | 5 mg |

The tablets are coated with a colored layer of sugar.

Example c

| | Capsule Formulation |
|---|---|
| Active substance* | 10 mg |
| Corn starch | 90 mg |
| Lactose | 50 mg |
| Talc | 2 mg |

This mixture is introduced into gelatin capsules.

Example d

| | Injection Solution |
|---|---|
| Active substance* | 12 mg |
| Sorbitol | 40 mg |
| Sterile water to | 1 ml |

Example e

| | Liquid Oral Formulation |
|---|---|
| Active substance* | 2 g |
| Saccharose | 250 g |
| Glucose | 300 g |
| d-Sorbitol | 150 g |
| Agar-agar | 0.15 g |
| Methylparaben | 0.5 g |
| Propylparaben | 0.05 g |
| Flavoring substance (orange flavor) | 10 g |
| Tartazin yellow | |
| Purified water to | 1000 ml |

Example f

| | Liquid Oral Formulation |
|---|---|
| Active substance* | 2 g |
| Tragacanth | 7 g |
| Glycerin | 50 g |
| Saccharose | 400 g |
| Methylparaben | 0.5 g |
| Propylparaben | 0.05 g |
| Flavoring substance (flavor of black currants) | 10 g |
| Red dye No. 2C.E. 184 | 0.02 g |
| Purified water to | 1000 ml |

Example g

| | Liquid Oral Formulation |
|---|---|
| Active substance* | 2.4 g |
| Saccharose | 400 g |
| Tincture of bitter orange peels | 20 g |
| Tincture of sweet orange peels | 15 g |
| Purified water to | 1000 ml |

The following sections respectively evidence that Avarone is effective in combination with other active compounds or principles; that its employment has no adverse effect upon the immune response of a subject treated therewith; and that an advantageous treatment regimen can be designed because of its extended half-life.

APPLICATION OF AVARONE IN COMBINATION WITH OTHER COMPOUNDS

It is also advantageous to use Avarone in combination with other compounds.

Example:

Combination studies were performed in vitro with Avarone together with diethyldithiocarbamate (DDC). DDC has previously been shown to have immunomodulating activity (Lang et al., Lancet 2: 1066; 1985) in AIDS patients and acts by inhibition of superoxide dismutase (SODase) both in vitro and in vivo (Heikkila et al., J. Biol. Chem. 251: 2182–2185; 1976 and Heikkila et al., In: Superoxide and Superoxide Dismutase (eds. A. M. Michelson, J. M. McCord and I. Friedovich), Academic Press, New York; pp. 367–373).

Methods:

L5178y mouse lymphoma cells were grown in roller tube cultures in Eagle's minimum essential medium, supplemented with 10% horse serum (Müller et al., Cancer Res. 39: 1102–1107; 1979 and Müller et al. Cancer Res. 45: 4822–4826; 1985). For the dose response experiments, 5 ml cultures were initiated by inoculation of 5000 cells/ml and incubated at 37 degrees C. for 72 hours; the controls had generation times of 10.4–10.6 hours. The cell growth was determined by cell count with a computer supported cell-counter (128-channel counter; Cytocomp, system Michaelis: BIOTRON-Medizinelektronik, Mainz; West Germany). The ED50 ($+/-$SD) was estimated by logit regression (L. Sachs, Angewandte Statistik, Springer-Verlag, Berlin 1984). The mathematical evaluation of the fractional inhibitory concentration indices (FIC indices) of Avarone-DDC combinations was performed according to published equations and experimental conditions (Müller et al., Cancer Lett. 1: 127–132; 1976; and Phillips et al., Antimicrob. Agents Chemother. 9: 736–740, 1976). FIC $>1$ are interpreted as antagonistic; FIC $=1$ as additive effects; FIC $<1$ as suggestive of synergism; and FIC $<0.5$ as significant synergism.

Results:

As a further proof for the additive effect of Avarone in combination with DDC, the FIC indices were determined.

Concentration ratios between 0.2:1 to 1.3:1.0 (Avarone:DDC) were chosen. The calculated FIC indices varied between 0.82 and 1.04 indicating an additive interaction between Avarone and DDC (Table).

Conclusion:

These studies show that Avarone can be administered in vitro in combination with other therapeutic agents resulting in a beneficial therapeutical effect.

Table

Fractional inhibitory concentration indices (FIC indices) for avarone-DDC combination on L5178y cells The standard incubation conditions (5 ml and 72 hours) were chosen. The combination ratios are based on x $\mu$M avarone to y $\mu$M DDC.

| Drug combination | Concentration ratio | FIC index |
| --- | --- | --- |
| Avarone:DDC | 0.2:1.0 | 0.92 |
|  | 0.4:1.0 | 1.04 |
|  | 0.7:1.0 | 0.97 |

In conclusion, from the foregoing, it is apparent that the present invention provides a novel method for the treatment and control of AIDS and ARC using Avarone and derivatives and/or precursors and/or prodrugs thereof, and pharmaceutical compositions embodying these active ingredients for the said intended use, all having the foregoing enumerated characteristics and advantages.

It is to be understood that the invention is not to be limited to the exact details of operation, or to the exact compositions, methods, procedures or embodiments shown and described, as obvious modifications and equivalents will be apparent to one skilled in the art, and the invention is therefore to be limited only by the full scope which can be legally accorded to the appended claims.

I claim:

1. A method of treating AIDS/ARC comprising the step of administering an effective anti-AIDS/ARC amount of avarone to a living animal body in need of said treatment.

2. The method of claim 1, wherein the living animal body is a human being.

* * * * *